US 6,599,323 B2

(12) United States Patent
Melican et al.

(10) Patent No.: US 6,599,323 B2
(45) Date of Patent: Jul. 29, 2003

(54) REINFORCED TISSUE IMPLANTS AND METHODS OF MANUFACTURE AND USE

(75) Inventors: Mora Carolynne Melican, Bridgewater, NJ (US); Yufu Li, Bridgewater, NJ (US); Kelly R. Brown, Hillsborough, NJ (US); Iksoo Chun, Flemington, NJ (US); John McAllen, III, Point Pleasent, NJ (US); Alireza Rezania, Hillsborough, NJ (US); Angelo G. Scopelianos, Whitehouse Station, NJ (US); Murty N. Vyakarnam, New York, NY (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/747,489

(22) Filed: Dec. 21, 2000

(65) Prior Publication Data
US 2002/0120348 A1 Aug. 29, 2002

(51) Int. Cl.[7] .................................................. A61F 2/36
(52) U.S. Cl. ............................. 623/23.72; 623/23.75; 424/426
(58) Field of Search .............................. 428/221, 297.4, 428/296.7, 297.1, 298.1, 299.4, 299.7, 304.4, 306.6, 307.3, 312.2, 312.6; 442/315, 333, 355, 370; 623/11.11, 66.1, 23.72, 23.75, 23.76; 424/422–426

(56) References Cited

U.S. PATENT DOCUMENTS

| 5,108,989 A | 4/1992 | Amento et al. ............... 514/12 |
| 5,147,400 A | 9/1992 | Kaplan et al. ................. 623/13 |
| 5,206,023 A | 4/1993 | Hunziker ..................... 424/423 |
| 5,455,041 A | 10/1995 | Genco et al. ................ 424/435 |

(List continued on next page.)

FOREIGN PATENT DOCUMENTS

| EP | 0955024 | 4/1910 |
| EP | 0274898 | 12/1987 |
| EP | 0562864 | 9/1993 |
| EP | 1064958 | 1/2001 |
| WO | WO 86/00533 | 1/1986 |
| WO | 0016381 | 4/1999 |

OTHER PUBLICATIONS

Thomas F. Deuel and Nan Zhang, "Growth Factors" in Principles of Tissue Engineering, Second Edition, Academic Press, 2000, pp. 129–141.

Sally R. Frenkel, Ph.D. and Paul E. Di Cesare, M.D., "Degradation and Repair of Articular Cartilage" in Frontiers in Bioscience, 4th ed., pp. 671–685, Oct. 15, 1999, pp. 1–32.

Keith J. Gooch et al., "Mechanical Forces and Growth Factors Utilized in Tissue Engineering" in Frontier in Tissue Engineerging, Pergamon, 1998, Chapter II.3, pp. 61–82.

John A. Koski, M.D. et al., "Meniscal Injury and Repair", Orthopedic Clinics of North American, vol. 31, No. 3, Jul. 2000, pp. 419–435.

(List continued on next page.)

Primary Examiner—David J. Isabella
Assistant Examiner—Urmi Chattopadhyay
(74) Attorney, Agent, or Firm—Nutter, McClennen & Fish LLP

(57) ABSTRACT

A biocompatible tissue implant, as well as methods for making and using such an implant, is provided. Preferably, the tissue implant is bioabsorbable. The tissue implant comprises one or more layers of a bioabsorbable polymeric foam having pores with an open cell structure. The tissue implant also includes a reinforcement component which contributes both to the mechanical and the handling properties of the implant. Preferably, the reinforcement component is bioabsorbable as well. The tissue implant provided can be used in connection with the surgical repair of soft tissue injury, such as injury to the pelvic floor.

26 Claims, 3 Drawing Sheets

U.S. PATENT DOCUMENTS

| | | | |
|---|---|---|---|
| 5,632,745 A | 5/1997 | Schwartz | 606/75 |
| 5,677,335 A | 10/1997 | Shalaby et al. | |
| 5,723,331 A | 3/1998 | Tubo et al. | 435/366 |
| 5,766,631 A | 6/1998 | Arnold | |
| 5,769,899 A | 6/1998 | Schwartz et al. | 623/18 |
| 5,786,217 A | 7/1998 | Tubo et al. | 435/402 |
| 5,842,477 A | 12/1998 | Naughton et al. | 128/898 |
| 5,891,558 A | 4/1999 | Bell et al. | 428/218 |
| 5,904,717 A | 5/1999 | Brekke et al. | 623/16 |
| 5,990,378 A | 11/1999 | Ellis | 623/11 |
| 6,001,352 A | 12/1999 | Boyan et al. | 424/93.7 |
| 6,001,394 A | 12/1999 | Daculsi et al. | 424/489 |
| 6,005,161 A | 12/1999 | Brekke et al. | 623/16 |
| 6,153,292 A | 11/2000 | Bell et al. | |

OTHER PUBLICATIONS

John A. Koski, M.D. et al., "Tissue–Engineered Ligament—Cells, Matrix, and Growth Factors" in Tissue Engineering in Orthopedic Surgery, vol. 31, No. 3, Jul. 2000, pp. 437–452.

Clemente Ibarra, M.D. et al. "Tissue–Engineering Meniscuc—Cells and Matrix", in Tissue Engineering in Orthopedic Surgery, vol. 31, No. 3, Jul. 2000, pp. 411–418.

REINFORCED TISSUE IMPLANTS AND METHODS OF MANUFACTURE AND USE

FIELD OF THE INVENTION

The present invention relates to bioabsorbable, porous, reinforced tissue engineered implant devices for use in the repair of soft tissue injury such as damage to the pelvic floor and methods for making such devices.

BACKGROUND OF THE INVENTION

Individuals can sometimes sustain an injury to tissue, such as musculoskeletal tissue, that requires repair by surgical intervention. Such repairs can be effected by suturing the damaged tissue, and/or by mating an implant to the damaged tissue. The implant may provide structural support to the damaged tissue, and it can serve as a substrate upon which cells can grow, thus facilitating more rapid healing.

One example of a fairly common tissue injury is damage to the pelvic floor. This is a potentially serious medical condition that may occur during childbirth or from complications thereof which can lead to sustaining an injury of the vesicovaginal fascia. Such an injury can result in a cystocele, which is a herniation of the bladder. Similar medical conditions include rectoceles (a herniation of the rectum), enteroceles (a protrusion of the intestine through the rectovaginal or vesicovaginal pouch), and enterocystoceles (a double hernia in which both the bladder and intestine protrude). These conditions can be serious medical problems that can severely and negatively impact a patient both physiologically and psychologically.

These conditions are usually treated by surgical procedures in which the protruding organs or portions thereof are repositioned. A mesh-like patch is often used to repair the site of the protrusion.

Although these patches are useful to repair some herniations, they are usually not suitable for pelvic floor repair. Moreover, patches or implants that are made from a non-bioabsorbable material can lead to undesirable tissue erosion and abrasion. Other implant materials, which are biologically derived (e.g., allografts and autografts), have disadvantages in that they can contribute to disease transmission, and they are difficult to manufacture in such a way that their properties are reproducible from batch to batch.

Various known devices and techniques for treating such conditions have been described in the prior art. For example, European Patent Application No. 0 955 024 A2 describes a intravaginal set, a medical device used to contract the pelvic floor muscles and elevate the pelvic floor.

In addition, Trip et al (WO 99 16381) describe a biocompatible repair patch having a plurality of apertures formed therein, which is formed of woven, knitted, nonknitted, or braided biocompatable polymers. This patch can be coated with a variety of bioabsorbable materials as well as another material that can decrease the possibility of infection, and/or increase biocompatibility.

Other reinforcing materials are disclosed in U.S. Pat. No. 5,891,558 (Bell et al) and European Patent Application No. 0 274 898 A2 (Hinsch). Bell et al describe biopolymer foams and foam constructs that can be used in tissue repair and reconstruction. Hinsch describes an open cell, foam-like implant made from resorbable materials, which has one or more textile reinforcing elements embedded therein. Although potentially useful, the implant material is believed to lack sufficient strength and structural integrity to be effectively used as a tissue repair implant.

Despite existing technology, there continues to be a need for a bioabsorbable tissue repair implant having sufficient structural integrity to withstand the stresses associated with implantation into an affected area.

SUMMARY OF THE INVENTION

This invention relates to bioabsorbable, porous, reinforced tissue implant, or "scaffold," devices for use in the repair or regeneration of diseased or damaged tissue, and the methods for making and using these devices. The implants comprise a bioabsorbable polymeric foam component having pores with an open cell pore structure. The foam component is reinforced with a material such as a mesh. Preferably, the implant has sufficient structural integrity to enable it to be handled in the operating room prior to and during implantation. These implants should also have sufficient properties (e.g., tear strength) to enable them to accept and retain sutures without tearing. Desirable properties are imparted to the implant of the invention by integrating the foam component with the reinforcement component. That is, the pore-forming webs or walls of the foam component penetrate the mesh of the reinforcement component so as to interlock therewith. The implant may include one or more layers of each of the foam and reinforcement components. Preferably, adjacent layers of foam are also integrated by at least a partial interlocking of the pore-forming webs or walls in the adjacent layers.

The reinforcement material is preferably a mesh, which may be bioabsorbable. The reinforcement should have a sufficient mesh density to permit suturing, but the density should not be so great as to impede proper bonding between the foam and the reinforcement. A preferred mesh density is in the range of about 12 to 80%.

The invention also relates to a method of preparing such biocompatible, bioabsorbable tissue implants. The implants are made by placing a reinforcement material within a mold in a desired position and orientation. A solution of a desired polymeric material in a suitable solvent is added to the mold and the solution is lyophilized to obtain the implant in which a reinforcement material is embedded in a polymeric foam.

The implant may be used as a tissue implant, such as to reinforce a patient's pelvic floor, or other soft tissue regions where a tear has contributed to herniation.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

The present invention relates to a biocompatible tissue implant or "scaffold" device which, preferably, is bioabsorbable, and to methods for making and using such a device. The implant includes one or more layers of a bioabsorbable polymeric foam having pores with an open cell pore structure. A reinforcement component is also present within the implant to contribute enhanced mechanical and handling properties. The reinforcement component is preferably in the form of a mesh fabric that is biocompatible. The reinforcement component may be bioabsorbable as well.

In some surgical applications, such as for use as a reinforcement material for repair of the pelvic floor, the tissue implants of the invention must be able to be handled in the operating room, and they must be able to be sutured without tearing. Additionally, the implants should have a burst strength adequate to reinforce the tissue, and the structure of the implant must be suitable to encourage tissue ingrowth. A preferred tissue ingrowth-promoting structure is one where the cells of the foam component are open and sufficiently sized to permit cell ingrowth. A suitable pore size is one in which the pores have an average diameter in the range of about 100 to 1000 microns and, more preferably, about 150 to 500 microns.

Figure 1:
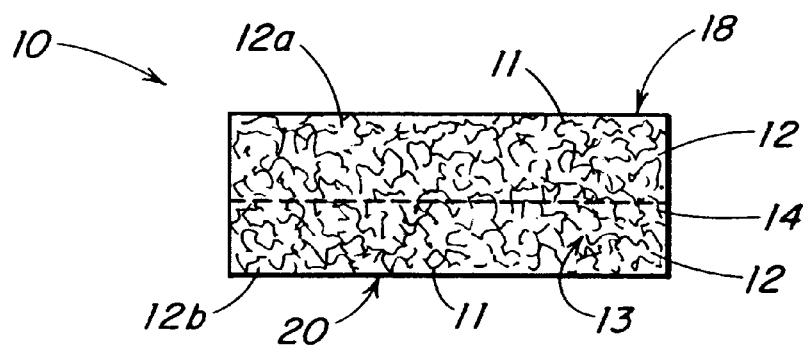
FIG. 1 is a sectional view of a tissue implant constructed according to the present invention.
Figure 2:
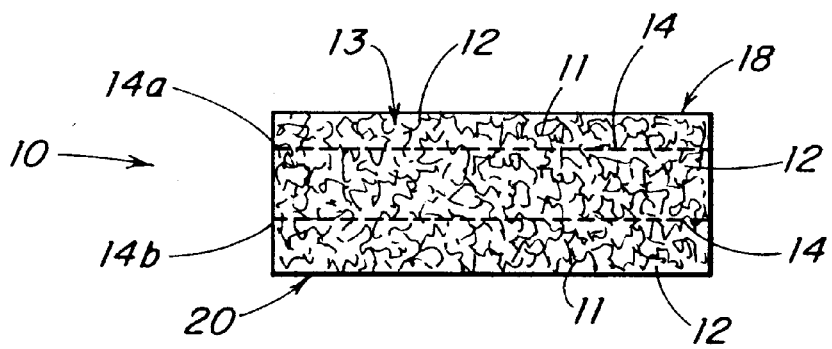
FIG. 2 is a sectional view of an alternative embodiment of the implant of the present invention.
Figure 3:
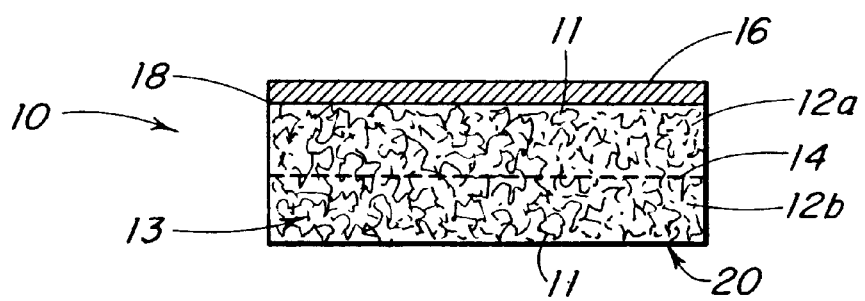
FIG. 3 is a sectional view of yet another embodiment of the implant of the present invention.

Referring to FIGS. 1 through 3, the implant 10 includes a polymeric foam component 12 and a reinforcement component 14. The foam component preferably has pores 13 with an open cell pore structure. Although illustrated as having the reinforcement component disposed substantially in the center of a cross section of the implant, it is understood that the reinforcement material can be disposed at any location within the implant. Further, as shown in FIG. 2, more than one layer of each of the foam component 12a, 12b and reinforcement component 14a, 14b may be present in the implant. It is understood that various layers of the foam component and/or the reinforcement material may be made from different materials.

FIG. 3 illustrates an embodiment in which a barrier layer 16 is present in the implant. Although illustrated as being only on one surface of the implant 10, the barrier layer 16 may be present on either or both of the top and bottom surfaces 18, 20 of the implant.

Figure 7:
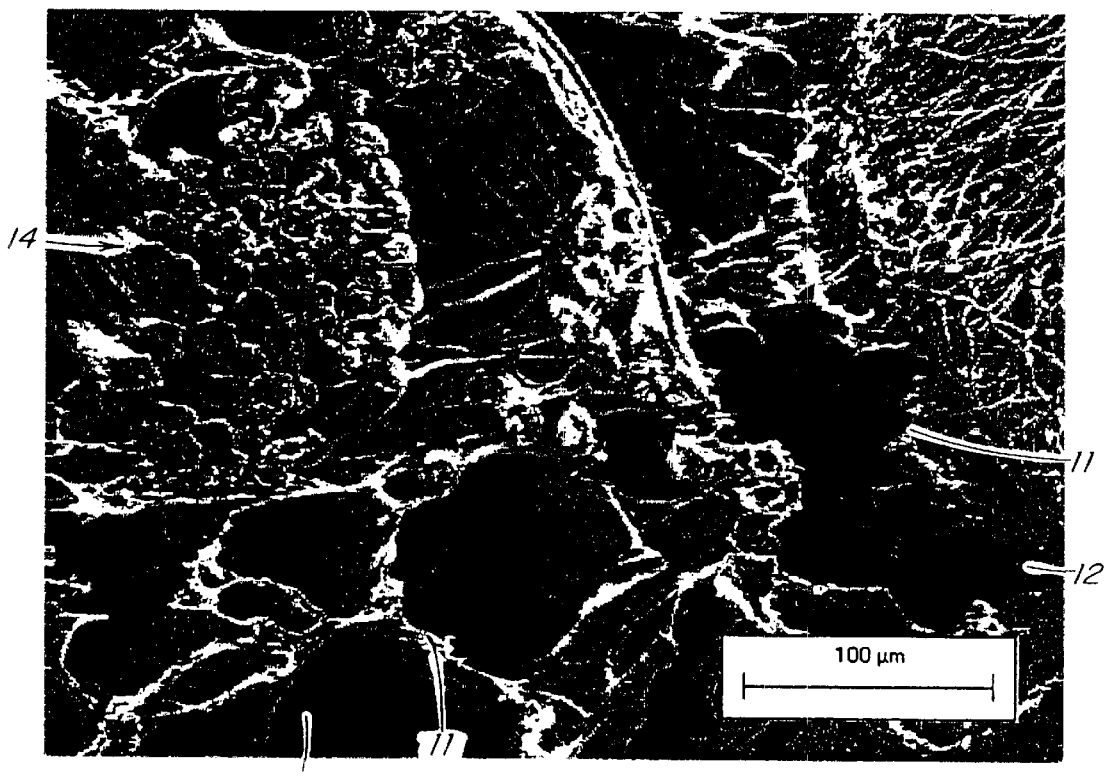
FIG. 7 is a scanning electron micrograph of a portion of an implant according to the present invention.

The implant 10 must have sufficient structural integrity and physical properties to facilitate ease of handling in an operating room environment, and to permit it to accept and retain sutures without tearing. Adequate strength and physical properties are developed in the implant through the selection of materials used to form the foam and reinforcement components, and the manufacturing process. As shown in FIG. 7, the foam component 12 is integrated with the reinforcement component 14 such that the web or walls 11 of the foam component that form pores 13 penetrate the mesh of the reinforcement component 14 and interlock with the reinforcement component. The pore-forming walls in adjacent layers of the foam component also interlock with one another, regardless of whether the foam layers are separated by a layer or reinforcement material or whether they are made from the same or different materials.

A variety of bioabsorbable polymers can be used to make porous, reinforced tissue engineered implant or scaffold devices according to the present invention. Examples of suitable biocompatible, bioabsorbable polymers include polymers selected from the group consisting of aliphatic polyesters, poly(amino acids), copoly(ether-esters), poly- alkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, $\alpha,\alpha$-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly (iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251–272 (1997). Copoly(ether-esters), for the purpose of this invention, are understood to include those copolyester-ethers as described in the Journal of Biomaterials Research, Vol. 22, pages 993–1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and $\in$-caprolactone such as are described by Allcock in *The Encyclopedia of Polymer Science*, Vol. 13, pages 31–41, Wiley Intersciences, John Wiley & Sons, 1988 and by Vandorpe, et al in the *Handbook of Biodegradable Polymers*, edited by Domb, et al, Hardwood Academic Press, pp. 161–182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99–118 (1997).

As used herein, the term "glycolide" is understood to include polyglycolic acid. Further, the term "lactide" is understood to include L-lactide, D-lactide, blends thereof, and lactic acid polymers and copolymers.

Currently, aliphatic polyesters are among the preferred absorbable polymers for use in making the foam implants according to the present invention. Aliphatic polyesters can be homopolymers, copolymers (random, block, segmented, tappered blocks, graft, triblock, etc.) having a linear, branched or star structure. Suitable monomers for making aliphatic homopolymers and copolymers may be selected from the group consisting of, but are not limited to, lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), δ-valerolactone, β-butyrolactone, ∈-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one, and combinations thereof.

Elastomeric copolymers are also particularly useful in the present invention. Suitable elastomeric polymers include those with an inherent viscosity in the range of about 1.2 dL/g to 4 dL/g, more preferably about 1.2 dL/g to 2 dL/g and most preferably about 1.4 dL/g to 2 dL/g as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In the preferred embodiments of this invention, the elastomer from which the foam component is formed exhibits a percent elongation (e.g., greater than about 200 percent and preferably greater than about 500 percent). In addition to these elongation and modulus properties, suitable elastomers should also have a tensile strength greater than about 500 psi, preferably greater than about 1,000 psi, and a tear strength of greater than about 50 lbs/inch, preferably greater than about 80 lbs/inch.

Exemplary bioabsorbable, biocompatible elastomers include but are not limited to elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ∈-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30); and blends thereof. Examples of suitable bioabsorbable elastomers are described in U.S. Pat. Nos. 4,045,418; 4,057,537 and 5,468,253.

In one embodiment the elastomer is a 35:65 copolymer of polyglycolic acid and polycaprolactone, formed in a dioxane solvent and including a polydioxanone mesh. In another embodiment, the elastomer is a 50:50 blend of a (35:65 coplymer of polyglycolic acid and polycaprolactone) and 40:60 ∈-caprolactone-co-lactide.

One of ordinary skill in the art will appreciate that the selection of a suitable polymer or copolymer for forming the foam depends on several factors. The more relevant factors in the selection of the appropriate polymer(s) that is used to form the foam component include bioabsorption (or biodegradation) kinetics; in vivo mechanical performance; cell response to the material in terms of cell attachment, proliferation, migration and differentiation; and biocompatibility. Other relevant factors, which to some extent dictate the in vitro and in vivo behavior of the polymer, include the chemical composition, spatial distribution of the constituents, the molecular weight of the polymer, and the degree of crystallinity.

The ability of the material substrate to resorb in a timely fashion in the body environment is critical. But the differences in the absorption time under in-vivo conditions can also be the basis for combining two different copolymers. For example, a copolymer of 35:65 ε-caprolactone and glycolide (a relatively fast absorbing polymer) is blended with 40:60 ε-caprolactone and L-lactide copolymer (a relatively slow absorbing polymer) to form a foam component. Depending upon the processing technique used, the two constituents can be either randomly inter-connected bicontinuous phases, or the constituents could have a gradient-like architecture in the form of a laminate type composite with a well integrated interface between the two constituent layers. The microstructure of these foams can be optimized to regenerate or repair the desired anatomical features of the tissue that is being engineered.

In one embodiment it is desireable to use polymer blends to form structures which transition from one composition to another composition in a gradient-like architecture. Foams having this gradient-like architecture are particularly advantageous in tissue engineering applications to repair or regenerate the structure of naturally occurring tissue such as cartilage (articular, meniscal, septal, tracheal, etc.), esophagus, skin, bone, and vascular tissue. For example, by blending an elastomer of ε-caprolactone-co-glycolide with ε-caprolactone-co-lactide (e.g., with a mole ratio of about 5:95) a foam may be formed that transitions from a softer spongy material to a stiffer more rigid material in a manner similar to the transition from cartilage to bone. Clearly, one of ordinary skill in the art will appreciate that other polymer blends may be used for similar gradient effects, or to provide different gradients (e.g., different absorption profiles, stress response profiles, or different degrees of elasticity). Additionally, these foam constructs can be used for organ repair replacement or regeneration strategies that may benefit from these unique tissue implants. For example, these implants can be used for spinal disc, cranial tissue, dura, nerve tissue, liver, pancreas, kidney, bladder, spleen, cardiac muscle, skeletal muscle, tendons, ligaments, and breast tissues.

The reinforcing component of the tissue implant of the present invention can be comprised of any absorbable or non-absorbable biocompatible material, including textiles with woven, knitted, warped knitted (i.e., lace-like), non-woven, and braided structures. In an exemplary embodiment the reinforcing component has a mesh-like structure. In any of the above structures, mechanical properties of the material can be altered by changing the density or texture of the material, or by embedding particles in the material. The fibers used to make the reinforcing component can be monofilaments, yarns, threads, braids, or bundles of fibers. These fibers can be made of any biocompatible material including bioabsorbable materials such as polylactic acid (PLA), polyglycolic acid (PGA), polycaprolactone (PCL), polydioxanone (PDO), trimethylene carbonate (TMC), polyvinyl alcohol (PVA), copolymers or blends thereof. In one embodiment, the fibers are formed of a polylactic acid and polyglycolic acid copolymer at a 95:5 mole ratio.

In another embodiment, the fibers that form the reinforcing material can be made of a bioabsorbable glass. Bioglass, a silicate containing calcium phosphate glass, or calcium phosphate glass with varying amounts of solid particles added to control resorption time are examples of materials that could be spun into glass fibers and used for the reinforcing material. Suitable solid particles that may be added include iron, magnesium, sodium, potassium, and combinations thereof.

The reinforcing material may also be formed from a thin, perforation-containing elastomeric sheet with perforations to allow tissue ingrowth. Such a sheet could be made of blends or copolymers of polylactic acid (PLA), polyglycolic acid (PGA), and polycaprolactone (PCL).

In one embodiment, filaments that form the reinforcing material may be co-extruded to produce a filament with a sheath/core construction. Such filaments are comprised of a sheath of biodegradable polymer that surrounds one or more cores comprised of another biodegradable polymer. Filaments with a fast-absorbing sheath surrounding a slower-absorbing core may be desirable in instances where extended support is necessary for tissue ingrowth.

One of ordinary skill in the art will appreciate that one or more layers of the reinforcing material may be used to reinforce the tissue implant of the invention. In addition, biodegradable reinforcing layers (e.g., meshes) of the same structure and chemistry or different structures and chemistries can be overlaid on top of one another to fabricate reinforced tissue implants with superior mechanical strength.

The foam component of the tissue implant may be formed as a foam by a variety of techniques well known to those having ordinary skill in the art. For example, the polymeric starting materials may be foamed by lyophilization, supercritical solvent foaming (i.e., as described in EP 464,163), gas injection extrusion, gas injection molding or casting with an extractable material (e.g., salts, sugar or similar suitable materials).

In one embodiment, the foam component of the engineered tissue implant devices of the present invention may be made by a polymer-solvent phase separation technique, such as lyophilization. Generally, however, a polymer solution can be separated into two phases by any one of the four techniques: (a) thermally induced gelation/crystallization; (b) non-solvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous structure of density less than the bulk polymer and pores in the micrometer ranges. See Microcellular Foams Via Phase Separation, J. Vac. Sci. Technolol., A. T. Young, Vol. 4(3), May/June 1986.

The steps involved in the preparation of these foams include choosing the right solvents for the polymers to be lyophilized and preparing a homogeneous solution. Next, the polymer solution is subjected to a freezing and vacuum drying cycle. The freezing step phase separates the polymer solution and vacuum drying step removes the solvent by sublimation and/or drying, leaving a porous polymer structure or an interconnected open cell porous foam.

Suitable solvents that may be used in the preparation of the foam component include, but are not limited to, formic acid, ethyl formate, acetic acid, hexafluoroisopropanol (HFIP), cyclic ethers (e.g., tetrahydrofuran (THF), dimethylene fluoride (DMF), and polydioxanone (PDO), acetone, acetates of C2 to C5 alcohols (e.g., ethyl acetate and t-butylacetate), glyme (e.g., monoglyme, ethyl glyme, diglyme, ethyl diglyme, triglyme, butyl diglyme and tetraglyme), methylethyl ketone, dipropyleneglycol methyl ether, lactones (e.g., γ-valerolactone, δ-valerolactone, β-butyrolactone, γ-butyrolactone), 1,4-dioxane, 1,3-dioxolane, 1,3-dioxolane-2-one (ethylene carbonate), dimethylcarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, a preferred solvent is 1,4-dioxane. A homogeneous solution of the polymer in the solvent is prepared using standard techniques.

The applicable polymer concentration or amount of solvent that may be utilized will vary with each system. Generally, the amount of polymer in the solution can vary from about 0.5% to about 90% and, preferably, will vary from about 0.5% to about 30% by weight, depending on factors such as the solubility of the polymer in a given solvent and the final properties desired in the foam.

In one embodiment, solids may be added to the polymer-solvent system to modify the composition of the resulting foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting tissue implant, thus causing compositional changes in all such regions. For example, concentration of solids in selected locations can be accomplished by adding metallic solids to a solution placed in a mold made of a magnetic material (or vice versa).

A variety of types of solids can be added to the polymer-solvent system. Preferably, the solids are of a type that will not react with the polymer or the solvent. Generally, the added solids have an average diameter of less than about 1.0 mm and preferably will have an average diameter of about 50 to about 500 microns. Preferably, the solids are present in an amount such that they will constitute from about 1 to about 50 volume percent of the total volume of the particle and polymer-solvent mixture (wherein the total volume percent equals 100 volume percent).

Exemplary solids include, but are not limited to, particles of demineralized bone, calcium phosphate particles, Bioglass particles or calcium carbonate particles for bone repair, leachable solids for pore creation and particles of bioabsorbable polymers not soluble in the solvent system that are effective as reinforcing materials or to create pores as they are absorbed, and non-bioabsorbable materials.

Suitable leachable solids include nontoxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. Such a process is described in U.S. Pat. No. 5,514,378. Preferably the foam will be dried after the leaching process is complete at low temperature and/or vacuum to minimize hydrolysis of the foam unless accelerated absorption of the foam is desired.

Suitable non-bioabsorbable materials include biocompatible metals such as stainless steel, coblat chrome, titanium and titanium alloys, and bioinert ceramic particles (e.g., alumina, zirconia, and calcium sulfate particles). Further, the non-bioabsorbable materials may include polymers such as polyethylene, polyvinylacetate, polymethylmethacrylate, silicone, polyethylene oxide, polyethylene glycol, polyurethanes, polyvinyl alcohol, natural biopolymers (e.g., cellulose particles, chitin, keratin, silk, and collagen particles), and fluorinable polymers and copolymers (e.g., polyvinylidene fluoride).

It is also possible to add solids (e.g., barium sulfate) that will render the tissue implants radio opaque. The solids that may be added also include those that will promote tissue regeneration or regrowth, as well as those that act as buffers, reinforcing materials or porosity modifiers.

As noted above, porous, reinforced tissue implant devices of the present invention are made by injecting, pouring, or otherwise placing, the appropriate polymer solution into a mold set-up comprised of a mold and the reinforcing elements of the present invention. The mold set-up is cooled in an appropriate bath or on a refrigerated shelf and then lyophilized, thereby providing a reinforced tissue engineered scaffold. In the course of forming the foam component, it is believed to be important to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogenous nucleation occurs. One of ordinary skill in the art can readily optimize the parameters without undue experimentation.

The required general processing steps include the selection of the appropriate materials from which the polymeric foam and the reinforcing components are made. If a mesh reinforcing material is used, the proper mesh density must be selected. Further, the reinforcing material must be properly aligned in the mold, the polymer solution must be added at an appropriate rate and, preferably, into a mold that is tilted at an appropriate angle to avoid the formation of air bubbles, and the polymer solution must be lyophilized.

In embodiments that utilize a mesh reinforcing material, the reinforcing mesh has to be of a certain density. That is, the openings in the mesh material must be sufficiently small to render the construct suturable, but not so small as to impede proper bonding between the foam and the reinforcing mesh as the foam material and the cells thereof penetrate the mesh openings. Without proper bonding the integrity of the layered structure is compromised leaving the construct fragile and difficult to handle.

During the lyophilization of the reinforced foam, several parameters and procedures are important to produce implants with the desired integrity and mechanical properties. Preferably, the reinforcement material is substantially flat when placed in the mold. To ensure the proper degree of flatness, the reinforcement (e.g., mesh) is pressed flat using a heated press prior to its placement within the mold. Further, in the event that reinforcing structures are not isotropic it is desirable to indicate this anisotropy by marking the construct to indicate directionality. This can be accomplished by embedding one or more indicators, such as dyed markings or dyed threads, within the woven reinforcements. The direction or orientation of the indicator will indicate to a surgeon the dimension of the implant in which physical properties are superior.

As noted above, the manner in which the polymer solution is added to the mold prior to lyophilization helps contribute to the creation of a tissue implant with adequate mechanical integrity. Assuming that a mesh reinforcing material will be used, and that it will be positioned between two thin (e.g., 0.75 mm) shims, it should be positioned in a substantially flat orientation at a desired depth in the mold. The polymer solution is poured in a way that allows air bubbles to escape from between the layers of the foam component. Preferably, the mold is tilted at a desired angle and pouring is effected at a controlled rate to best prevent bubble formation. One of ordinary skill in the art will appreciate that a number of variables will control the tilt angle and pour rate. Generally, the mold should be tilted at an angle of greater than about 1 degree to avoid bubble formation. In addition, the rate of pouring should be slow enough to enable any air bubbles to escape from the mold, rather than to be trapped in the mold.

If a mesh material is used as the reinforcing component the density of the mesh openings is an important factor in the formation of a resulting tissue implant with the desired mechanical properties. A low density, or open knitted mesh material, is preferred. One particularly preferred material is a 90/10 copolymer of PGA/PLA, sold under the tradename VICRYL (Ethicon, Inc., Somerville, N.J.). One exemplary low density, open knitted mesh is Knitted VICRYL VKM-M, available from Ethicon, Inc., Somerville, N.J.

The density or "openness" of a mesh material can be evaluated using a digital photocamera interfaced with a computer. In one evaluation, the density of the mesh was determined using a Nikon SMZ-U Zoom with a Sony digital photocamera DKC-5000 interfaced with an IBM 300PL computer. Digital images of sections of each mesh magnified to 20× were manipulated using Image-Pro Plus 4.0 software in order to determine the mesh density. Once a digital image was captured by the software, the image was thresholded such that the area accounting for the empty spaces in the mesh could be subtracted from the total area of the image. The mesh density was taken to be the percentage of the remaining digital image. Implants with the most desireable mechanical properties were found to be those with a mesh density in the range of about 12 to 80% and more preferably about 45 to 80%.

Figure 4:
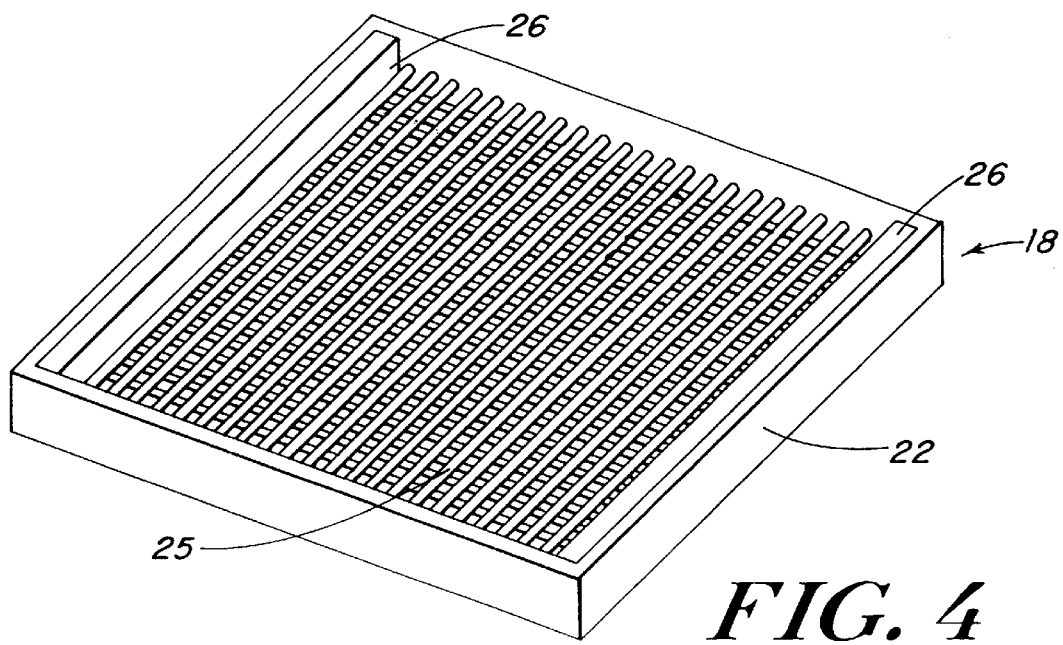
FIG. 4 is a perspective view of one embodiment of a mold set-up useful with the present invention.
Figure 5:
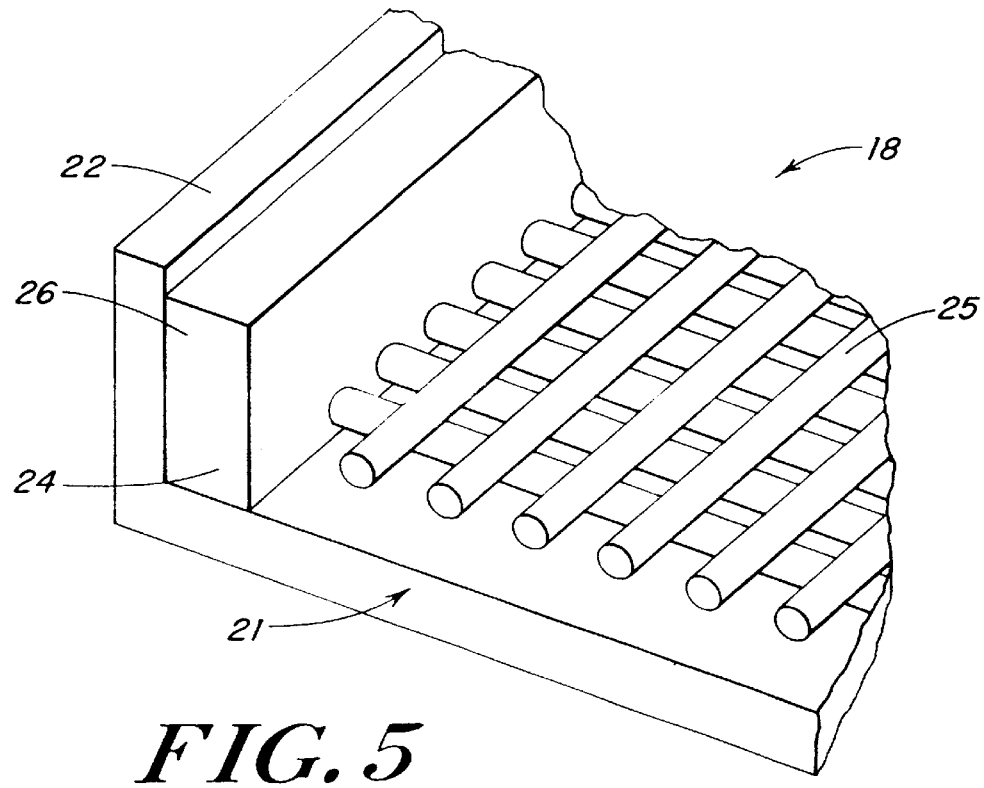
FIG. 5 is a sectional view of a portion of the mold set-up of FIG. 4.

FIGS. 4 and 5 illustrate a mold set up useful with the present invention in which mold 18 has a base 21 and side walls 22. Bottom shims 24 are disposed parallel to each other on an upper surface of base 21. Although parallel alignment of bottom shims 24 is illustrated, any number of shims, as well as any desired alignment, may be utilized. As further illustrated, reinforcing fabric 25 is placed over the bottom shims 24, and held in place by top shims 26, that are disposed parallel to each other on the reinforcing fabric 25. Though not shown, reinforcing fabric 25 can be placed between the bottom shims 24 and top shims 26 in a variety of ways. In one embodiment, the height of the bottom shims 24 can be varied so the mesh is placed nearer the top or bottom surface of the sandwich construct.

In another embodiment, an electrostatically spun fabric barrier may be added to act as a barrier to hyperplasia and tissue adhesion, thus reducing the possibility of postsurgical adhesions. The fabric barrier is preferably in the form of dense fibrous fabric that is added to the implant. Preferably, the fibrous fabric is comprised of small diameter fibers that are fused to the top and/or bottom surface of the foam component. This enables certain surface properties of the structure, such as porosity, permeability, degradation rate and mechanical properties, to be controlled.

One of ordinary skill in the art will appreciate that the fibrous fabric can be produced via an electrostatic spinning process in which a fibrous layer can be built up on a lyophilized foam surface. This electrostatic spinning process may be conducted using a variety of fiber materials. Exemplary fiber materials include aliphatic polyesters. A variety of solvents may be used as well, including those identified above that are useful to prepare the polymer solution that forms the foam component.

The composition, thickness, and porosity of the fibrous layer may be controlled to provide the desired mechanical and biological characteristics. For example, the bioabsorption rate of the fibrous layer may be selected to provide a longer or shorter bioabsorption profile as compared to the underlying foam layer. Additionally, the fibrous layer may provide greater structural integrity to the composite so that mechanical force may be applied to the fibrous side of the structure. In one embodiment the fibrous layer could allow the use of sutures, staples or various fixation devices to hold the composite in place. Generally, the fibrous layer has a thickness in the range of about 1 micron to 1000 microns.

One possible application of a tissue implant device with a fibrous surface layer is as a matrix for pelvic floor repair. The various components in such an implant serve different functions. The reinforced foam layer encourages the ingrowth and proliferation of cells, and the fibrous layer, with a decreased permeability, and provides a barrier to cellular infiltration. The lyophilized foam structure can be optimized for cell infiltration by smooth muscle cells or fibroblasts. The fibrous fabric layer also allows the diffusion of nutrients and waste products while limiting the migration of the cells into the implant, and would assist in the prevention of postsurgical adhesions.

The following examples are illustrative of the principles and practice of this invention. Numerous additional embodiments within the scope and spirit of the invention will become apparent to those of ordinary skill in the art.

EXAMPLE 1

This example describes the preparation of three-dimensional elastomeric tissue implants with and without a reinforcement in the form of a biodegradable mesh.

A solution of the polymer to be lyophilized to form the foam component was prepared in a four step process. A 95/5 weight ratio solution of 1,4-dioxane/(40/60 PCL/PLA) was made and poured into a flask. The flask was placed in a water bath, stirring at 70° C. for 5 hrs. The solution was filtered using an extraction thimble, extra coarse porosity, type ASTM 170-220 (EC) and stored in flasks.

Figure 6:
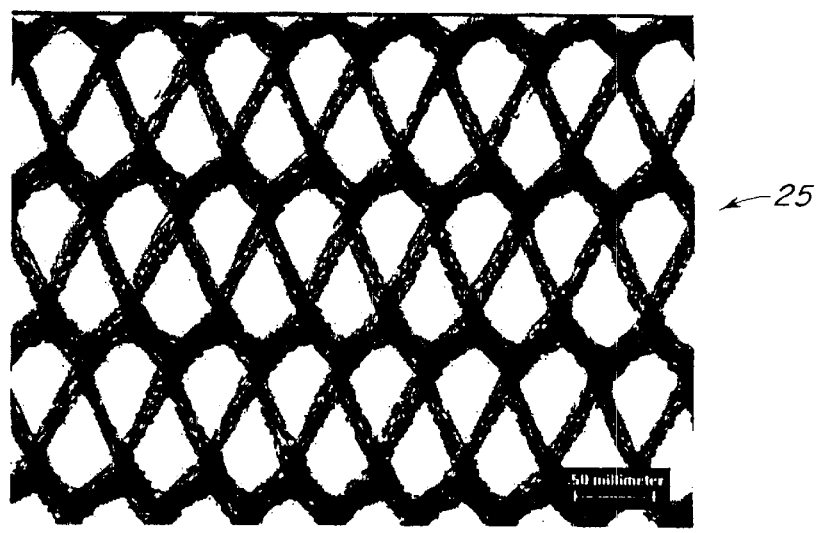
FIG. 6 is a scanning electron micrograph of a bioabsorbable knitted mesh reinforcement material useful with the implant of the present invention.

Reinforcing mesh materials formed of a 90/10 copolymer of polyglycolic/polylactic acid (PGA/PLA) knitted (Code VKM-M) and woven (Code VWM-M), both sold under the tradename VICRYL were rendered flat by ironing, using a compression molder at 80° C./2 min. FIG. 6 is a scanning electron micrograph (SEM) of the knitted mesh. After preparing the meshes, 0.8-mm shims were placed at each end of a 15.3×15.3 cm aluminum mold, and the mesh was sized (14.2 mm) to fit the mold. The mesh was then laid into the mold, covering both shims. A clamping block was then placed on the top of the mesh and the shim such that the block was clamped properly to ensure that the mesh had a uniform height in the mold. Another clamping block was then placed at the other end, slightly stretching the mesh to keep it even and flat.

As the polymer solution was added to the mold, the mold was tilted to about a 5 degree angle so that one of the non-clamping sides was higher than the other. Approximately 60 ml of the polymer solution was slowly transferred into the mold, ensuring that the solution was well dispersed in the mold. The mold was then placed on a shelf in a Virtis, Freeze Mobile G freeze dryer. The following freeze drying sequence was used: 1) 20° C. for 15 minutes; 2) −5° C. for 120 minutes; 3) −5° C. for 90 minutes under vacuum 100 milliTorr; 4) 5° C. for 90 minutes under vacuum 100 milliTorr; 5) 20° C. for 90 minutes under vacuum 100 milliTorr. The mold assembly was then removed from the freezer and placed in a nitrogen box overnight. Following the completion of this process the resulting implant was carefully peeled out of the mold in the form of a foam/mesh sheet.

Nonreinforced foams were also fabricated. To obtain non-reinforced foams, however, the steps regarding the insertion of the mesh into the mold were not performed. The lyophilization steps above were followed.

FIG. 7 is a scanning electron micrograph of a portion of an exemplary mesh-reinforced foam tissue implant formed by this process. The pores in this foam have been optimized for cell ingrowth.

EXAMPLE 2

Lyophilized 40/60 polycaprolactone/polylactic acid, (PCL/PLA) foam, as well as the same foam reinforced with an embedded VICRYL knitted mesh, were fabricated as described in Example 1. These reinforced implants were tested for suture pull-out strength and burst strength and compared to both standard VICRYL mesh and non-reinforced foam prepared following the procedure of Example 1.

Specimens were tested both as fabricated, and after in vitro exposure. In vitro exposure was achieved by placing the implants in phosphate buffered saline (PBS) solutions held at 37° C. in a temperature controlled waterbath.

For the suture pull-out strength test, the dimension of the specimens was approximately 5 cm×9 cm. Specimens were tested for pull-out strength in the wale direction of the mesh (knitting machine axis). A size 0 polypropylene monofilament suture (Code 8834H), sold under the tradename PROLENE (by Ethicon, Inc., Somerville, N.J.) was passed through the mesh 6.25 mm from the edge of the specimens. The ends of the suture were clamped into the upper jaw and the mesh or the reinforced foam was clamped into the lower jaw of an Instron model 4501. The Instron machine, with a 20 lb load cell, was activated using a cross-head speed of 2.54 cm per minute. The ends of the suture were pulled at a constant rate until failure occurred. The peak load (lbs) experienced during the pulling was recorded.

The results of this test are shown below in Table 1.

TABLE 1

| | Suture Pull-Out Data (lbs) | | |
| --- | --- | --- | --- |
| Time | Foam | Mesh | Foamed Mesh |
| 0 Day | 0.46 | 5.3 +/− 0.8 | 5.7 +/− 0.3 |
| 7 Day | — | 4.0 +/− 1.0 | 5.0 +/− 0.5 |

For the burst strength test, the dimension of the specimens was approximately 15.25 cm×15.25 cm. Specimens were tested on a Mullen tester (Model J, manufactured by B. F. Perkins, a Stendex company, a division of Roehlen Industries, Chicopee, Mass.). The test followed the standard operating procedure for a Mullen tester. Results are reported as pounds per square inch (psi) at failure.

The results of the burst strength test are shown in Table 2.

TABLE 2

Burst Strength Data (psi)

| Time | Point-Knitted VICRYL Mesh | Foamed Knitted Mesh |
| --- | --- | --- |
| 0 Day | 1349.5 | 1366.8 |
| 7 Day | 1109.4 | 1279.6 |

EXAMPLE 3

Mesh reinforced foam implants were implanted in an animal study and compared to currently used pelvic floor repair materials. The purpose of this animal study was to evaluate the subcutaneous tissue reaction and absorption of various polymer scaffolds. The tissue reaction and absorption was assessed grossly and histologically at 14 and 28 days post-implantation in the dorsal subcutis. In addition, the effect of these scaffolds on the bursting strength of incisional wounds in the abdominal musculature was determined. Burst testing was done at 14 and 28 days on ventrally placed implants and the attached layer of abdominal muscle.

Lyophilized 40/60 polycaprolactone/polylactic acid (PCL/PLA) foam, as well as the same foam reinforced with an embedded VICRYL knitted mesh were fabricated as described in Example 1. The foam and mesh reinforced foam implant were packaged and sterilized with ethylene oxide gas following standard sterilization procedures. Controls for the study included: a VICRYL mesh control, a mechanical control (No mesh placed), and a processed porcine corium, sold under the tradename DermMatrix (by Advanced UroScience, St. Paul, Minn.) control.

The animals used in this study were female Long-Evans rats supplied by Harlan Sprague Dawley, Inc. (Indianapolis, Ind.) and Charles River Laboratories (Portage, Mich.). The animals weighed between 200 and 350 g. The rats were individually weighed and anesthetized with an intraperitoneal injection of a mixture of ketamine hydrochloride (sold under the tradename KETASET, manufactured for Aveco Co., Inc., Fort Dodge, Iowa, by Fort Dodge Laboratories, Inc., Fort Dodge, Iowa,) (dose of 60 milligram/kg animal weight) and xylazine hydrochloride (sold under the tradename XYLAZINE, Fermenta Animal Health Co., Kansas City, Mo.) (dose of 10 milligrams/kg animal weight). After induction of anesthesia, the entire abdomen (from the forelimbs to the hindlimbs) and dorsum (from the dorsal cervical area to the dorsal lumbosacral area) was clipped free of hair using electric animal clippers. The abdomen was then scrubbed with chlorhexidine diacetate, rinsed with alcohol, dried, and painted with an aqueous iodophor solution of 1% available iodine. The anesthetized and surgically prepared animal was transferred to the surgeon and placed in a supine position. Sterile drapes were applied to the prepared area using aseptic technique.

A ventral midline skin incision (approximately 3–4 cm) was made to expose the abdominal muscles. A 2.5 cm incision was made in the abdominal wall, approximately 1 cm caudal to the xyphoid. The incision was sutured with size 3-0 VICRYL suture in a simple continuous pattern. One of the test articles, cut to approximately 5 cm in diameter, was placed over the sutured incision and 4 corner tacks were sutured (size 5-0 PROLENE) to the abdominal wall at approximately 11:00, 1:00, 5:00 and 7:00 o'clock positions. The skin incision was closed with skin staples or metal wound clips.

After the surgeon completed the laparotomy closure, mesh implant, and abdominal skin closure, the rat was returned to the prep area and the dorsum was scrubbed, rinsed with alcohol, and wiped with iodine as described previously for the abdomen. Once the dorsum was prepped, the rat was returned to a surgeon and placed in the desired recumbent position for dorsal implantation. A transverse skin incision, approximately 2 cm in length, was made approximately 1 cm caudal to the caudal edge of the scapula. A pocket was made in the dorsal subcutis by separating the skin from the underlying connective tissue via transverse blunt dissection. One of the test materials cut to approximately 2.0×2.0 cm square, was then inserted into the pocket and the skin incision closed with skin staples or metal wound clips.

Each animal was observed daily after surgery to determine its health status on the basis of general attitude and appearance, food consumption, fecal and urinary excretion and presence of abnormal discharges. All animals were also observed twice daily for the first three days after surgery for the presence of pain or discomfort and given.

The animals utilized in this study were handled and maintained in accordance with current requirements of the Animal Welfare Act. Compliance with the above Public Laws was accomplished by adhering to the Animal Welfare regulations (9 CFR) and conforming to the current standards promulgated in the Guide for the Care and Use of Laboratory Animals.

For the histopathology study, the rats were sacrificed after two weeks or four weeks, and the dorsal subcutaneous implant was removed, trimmed, and fixed in 10% neutral buffered Formalin (20× the tissue volume). The samples were processed in paraffin, cut into 5 mm sections, and stained with Hematoxylin Eosin (H & E).

Dorsal samples for tissue reaction assessment were cut to approximate 2.0 cm squares. Ventral samples for burst testing were cut to approximate 5.0 cm diameter circles.

The bursting strength of each specimen was measured together with the attached underlying abdominal muscle layer following the method of Example 2. The results of the burst strength tests are shown in Table 3.

TABLE 3

Burst Strength (psi)

| Sample | 14 Days | 28 Days |
| --- | --- | --- |
| Mesh Reinforced Foam | 81.8 +/− 17.3 | 73 +/− 4.5 |
| Dermatrix | 70 +/− 4.0 | 70* |

*Standard deviation is not available since only one sample survived until explant.

The histopathology study showed the mesh reinforced foam constructs had the highest degree of fibrous ingrowth and most robust encapsulation of all the implants tested at both time points. This fibrous reaction was mild in extent at 28 days.

EXAMPLE 4

This example describes another embodiment of the present invention in which the preparation of a hybrid structure of a mesh reinforced foam with a fabric composed of microfibrous is described.

A knitted VICRYL mesh reinforced foam of 60/40 PLA/PCL was prepared as described in Example 1. a sheet, 2.54 cm×6.35 cm, was attached on a metal plate connected with a ground wire. The sheet was then covered with microfibrous bioabsorbable fabric produced by an electrostatic spinning process. The electrostatically spun fabric provides resistance to cell prevention from surrounding tissues and it enhances the sutureability of the implant.

A custom made electrostatic spinning machine located at Ethicon Inc (Somerville, N.J.) was used for this experiment. A Spellman high voltage DC supply (Model No.: CZE30PN1000, Spellman High Voltage Electronics Corporation, Hauppauge, N.Y.) was used as high voltage source. Applied voltage as driving force and the speed of mandrel were controlled by the visal basic computer software. Distance between the spinneret and the plate was mechanically controlled.

A 14% solution of a 60/40 PLA/PCL copolymer produced at Corporate Biomaterials Center, a Division of Ethicon. Inc, Somerville, N.J. was prepared in trichloroethane chloride (TEC) solvent. The polymer solution was placed into a spinneret and high voltage was applied to the polymer solution. This experiment was performed at ambient temperature and humidity. The operating conditions during spinning were as follows:

| | |
|---|---|
| Spinneret voltage: | 25,000 V |
| Plate voltage: | Grounded |
| Spinneret to mandrel distance: | 15 cm |

This process resulted in a deposited porous elastomeric polymer of approximately 10–500 μm in thickness on surface of the mesh reinforced foam.

EXAMPLE 5

Peel test specimens of mesh reinforced foam were made so as to separate otherwise bonded layers at one end to allow initial gripping required for a T-peel test (ref. ASTM D1876-95).

Copolymer foams of 40/60 polycaprolactone/polylactic acid (PCL/PLA), reinforced with both 90/10 copolymer of polyglycolic/polylactic acid (PGA/PLA) knitted (Code VKM-M) and woven (Code VWM-M) meshes, were fabricated as described in Example 1. Test specimens strips, 2.0 cm×11.0 cm, were cut from the reinforced foam. Due to the cost of labor and materials, the size of the specimens was less than that cited in the above ASTM standard. The non-bonded section for gripping was produced by applying an aluminum foil blocker at one end to inhibit the penetration of polymer solution through the mesh reinforcement. The specimens were tested in an Instron Model 4501 Electromechanical Screw Test Machine. The initial distance between grips was 2.0 cm. The cross-head speed for all tests was held constant at 0.25 cm/min. The number of specimens of each construct tested was five.

The knitted VICRYL mesh foamed specimens required less force (0.087+/−0.050 in*lbf) to cause failure than did the woven VICRYL foamed specimens (0.269+/−0.054 in*lbf). It is important to note that the mode of failure in the two constructs was different. In the woven mesh specimens, there was some evidence of peel, whereas in the knitted mesh specimens, there was none. In fact, in the knitted specimens there was no sign of crack propagation at the interface between layers. A rate dependency in peel for the woven mesh specimens was noted. The test rate of 0.25 cm/min was chosen due to the absence of peel and swift tear of the foam at higher separation rates. Test results reported herein consist of tests run at this crosshead speed for both types of mesh. A slower speed of 0.025 cm/min was tried for the knitted mesh construct to investigate the possible onset of peel at sufficiently low separation speeds. However, the slower speed did not result in any change in the mode of failure.

In conclusion, the higher density of the woven mesh inhibited extensive penetration of polymeric foam and resulted in the dissipation of energy through the peeling of the foam from the mesh when subjected to a T-peel test at a cross-head speed of 0.25 cm/min. In the case of the lower density knitted mesh construct, there appeared to be little to no separation of foam from the mesh. In these experiments it appeared that the load was wholly dissipated by the cohesive tearing of the foam.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A biocompatible tissue implant, comprising:
   a bioabsorbable polymeric foam component having pores with an open cell pore structure; and
   a reinforcing component formed of a biocompatible, mesh-containing material having a mesh density in the range of about 12 to 80%,
   the foam component being integrated with the reinforcing component such that the pores of the foam component penetrate the mesh of the reinforcing component and interlock with the reinforcing component.

2. The implant of claim 1, wherein the foam component is present in one or more layers.

3. The implant of claim 2, wherein the layers of foam component are adjacent each other, the adjacent foam layers being integrated with one another by at least a partial interlocking of pore-forming webs of the foam.

4. The implant of claim 3, wherein the layers of the foam component are constructed of two or more different polymers.

5. The implant of claim 4, wherein the foam component has physical properties that vary across a thickness of the implant.

6. The implant of claim 1, wherein the reinforcing component is present in one or more layers.

7. The implant of claim 1, wherein the foam component is formed from a polymer selected from the group consisting of aliphatic polyesters, poly(amino acids), copoly(etheresters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, collagen, elastin, bioabsorbable starches, and combinations thereof.

8. The implant of claim 7, wherein the foam component is formed from aliphatic polyesters that are homopolymers or copolymers selected from the group consisting of lactides, glycolides, ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one, 1,5-dioxepan-2-one, 6,6-dimethyl-1,4-dioxan-2-one, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, and combinations thereof.

9. The implant of claim 1, wherein the foam component is formed from an elastomeric copolymer selected from the group consisting of ε-caprolactone-co-glycolide, ε-caprolactone-co-lactide, p-dioxanone (1,4-dioxan-2-one)-co-lactide, ε-caprolactone-co-p-dioxanone, p-dioxanone-co-trimethylene carbonate, trimethylene carbonate-co-glycolide, trimethylene carbonate-co-and lactide, and combinations thereof.

10. The implant of claim 1, wherein the polymer from which the foam component is constructed has a percent elongation greater than about 200.

11. The implant of claim 10, wherein the polymer from which the foam component is constructed has a tensile strength greater than about 500 psi.

12. The implant of claim 11, wherein the polymer from which the foam component is constructed has a tear strength greater than about 50 lbs/inch.

13. The implant of claim 1, wherein the reinforcing component is bioabsorbable.

14. The implant of claim 1, wherein the reinforcing component comprises a mesh-like material having a solid component with a plurality of openings formed therein.

15. The implant of claim 14, wherein the solid component of the mesh is formed from fibers made from a material selected from the group consisting of polylactic acid, polyglycolic acid, polycaprolactone, polydioxanone, trimethylene carbonate, polyvinyl alcohol, copolymers thereof, and combinations thereof.

16. The implant of claim 15, wherein the fibers are formed of a 90/10 copolymer of polyglycolic acid and polylactic acid.

17. The implant of claim 15, wherein the fibers are formed of a 95/5 copolymer of polylactic acid and polyglycolic acid.

18. The implant of claim 14, wherein the solid component of the mesh is formed from fibers made from a material selected from the group consisting of bioabsorbable silicate glass, bio absorbable calcium phosphate glass, and combinations thereof.

19. The implant of claim 18, wherein the fibers are selected from the group consisting of bioabsorbable silicate glass and bioabsorbable calcium phosphate glass and the solid component further comprises from about 1 to 50 percent by volume of an element selected from the group consisting of iron, sodium, magnesium, potassium, and combinations thereof.

20. The implant of claim 14, wherein the solid component is made of coextruded fibers having a core made of a first bioabsorbable polymer that is biologically resorbable at a first rate and that is surrounded by a sheath formed of a second bioabsorbable polymer that is biologically resorbable at a second, different rate.

21. The implant of claim 1, further comprising a fabric barrier layer formed on at least one surface of the implant.

22. The implant of claim 21, wherein the fabric barrier is formed on a top surface and a bottom surface of the implant.

23. The implant of claim 21, wherein the fabric barrier is a dense, fibrous fabric that is effective as a barrier to hyperplasia and tissue adhesion.

24. The implant of claim 23, wherein the fabric barrier is formed of an electrostatically spun aliphatic polyester.

25. A method of repairing a tissue tear, comprising:
   providing a biocompatible tissue implant comprising a bioabsorbable polymeric foam component having pores with an open cell pore structure and
   a reinforcing component formed of a biocompatible, mesh-containing material having a mesh density in the range of about 12 to 80%, wherein the foam component is integrated with the reinforcement component such that the pores of the foam component penetrate the mesh of the reinforcing component and interlock with the reinforcing component;
   placing the implant in a desired position relative to the tissue tear; and
   suturing the implant in the desired position.

26. The method of claim 25, wherein the implant is bioabsorbable.

* * * * *